United States Patent
Kastler et al.

(10) Patent No.: US 8,367,717 B2
(45) Date of Patent: Feb. 5, 2013

(54) HIGH PERFORMANCE SOLUTION PROCESSABLE SEMICONDUCTOR BASED ON DITHIENO [2,3-D:2', 3'-D']BENZO[1,2-B:4,5-B'] DITHIOPHENE

(75) Inventors: Marcel Kastler, Mannheim (DE); Silke Koehler, Mannheim (DE); Klaus Muellen, Cologne (DE); Peng Gao, Mainz (DE); Dirk Beckmann, Harxheim (DE); Xinliang Feng, Mainz (DE); Hoi Nok Tsao, Mainz (DE)

(73) Assignees: BASF SE, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 121 days.

(21) Appl. No.: 13/002,208

(22) PCT Filed: Jun. 25, 2009

(86) PCT No.: PCT/EP2009/057985
§ 371 (c)(1), (2), (4) Date: Dec. 30, 2010

(87) PCT Pub. No.: WO2010/000670
PCT Pub. Date: Jan. 7, 2010

(65) Prior Publication Data
US 2011/0155248 A1    Jun. 30, 2011

(30) Foreign Application Priority Data

Jul. 2, 2008 (EP) .................................. 08159525

(51) Int. Cl.
*A61K 31/38* (2006.01)
*C07D 333/50* (2006.01)
(52) U.S. Cl. ........................................ 514/443; 549/41
(58) Field of Classification Search .................. 514/443; 549/41
See application file for complete search history.

(56) References Cited

U.S. PATENT DOCUMENTS

| 4,423,995 | A | 1/1984 | Karis |
| 5,198,153 | A | 3/1993 | Angelopoulos et al. |
| 7,605,394 | B2 | 10/2009 | Marks et al. |
| 7,678,463 | B2 | 3/2010 | Marks et al. |

FOREIGN PATENT DOCUMENTS

| EP | 0 067 782 | 12/1982 |
| EP | 0 528 662 | 2/1993 |
| JP | 2008 10541 | 1/2008 |
| JP | 2009 54810 | 3/2009 |
| WO | 96 21659 | 7/1996 |
| WO | 2007 068618 | 6/2007 |
| WO | 2008 026602 | 3/2008 |
| WO | 2009 016107 | 2/2009 |

OTHER PUBLICATIONS

U.S. Appl. No. 13/140,595, filed Jun. 17, 2011, Mishra, et al.
Lin, Y-Y et al., "Pentacene-Based Organic Thin-Film Transistors", IEEE Transactions on Electron Devices, vol. 44, No. 8, pp. 1325-1331, XP 011016214, ISSN: 0018-9383, (Aug. 1, 1997).
Park, S. K. et al., "High Mobility Solution-Processed OTFTs", IEEE International Electron Devices Meeting Technical Digest, pp. 113-116, (Dec. 5-7, 2005).
International Search Report issued Aug. 19, 2009 in PCT/EP09/057985 filed Jun. 25, 2009.
U.S. Appl. No. 13/002,392, filed Jan. 3, 2011, Kastler, et al.
U.S. Appl. No. 13/002,425, filed Jan. 3, 2011, Kastler, et al.
U.S. Appl. No. 13/056,987, filed Feb. 1, 2011, Kastler, et al.
U.S. Appl. No. 13/128,961, filed Jan. 3, 2011, Quinn, et al.
U.S. Appl. No. 13/002,208, filed Dec. 30, 2010, Kastler, et al.
U.S. Appl. No. 13/376,296, filed Dec. 5, 2012, Mishra, et al.
U.S. Appl. No. 13/378,069, filed Dec. 14, 2011, Kastler, et al.

*Primary Examiner* — Taofiq A Solola
(74) *Attorney, Agent, or Firm* — Oblon, Spivak, McClelland, Maier & Neustadt, L.L.P.

(57) ABSTRACT

Dithienobenzodithiophenes of general formula (I) in which $R^1$ to $R^6$ are each independently selected from a) H, b) halogen, c) —CN, d) —NO$_2$, e) —OH, f) a $C_{1-20}$ alkyl group, g) a $C_{2-20}$ alkenyl group, h) a $C_{2-20}$ alkynyl group, i) a $C_{1-20}$ alkoxy group, j) a $C_{1-20}$ alkylthio group, k) a $C_{1-20}$ haloalkyl group, l) a —Y—$C_{3-10}$ cycloalkyl group, m) a —Y—$C_{6-14}$ aryl group, n) a —Y-3-12 membered cyclo-heteroalkyl group, or o) a —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cyc-loheteroalkyl group, and the 5-14 membered heteroaryl group is optionally substituted with 1-4 $R^7$ groups, wherein $R^1$ and $R^3$ and $R^2$ and $R^4$ may also together form an aliphatic cyclic moiety, Y is independently selected from divalent a $C_{1-6}$ alkyl group, a divalent $C_{1-6}$ haloalkyl group, or a covalent bond; and m is independently selected from 0, 1, or 2. The invention also relates to the use of the dithienobenzodithiophenes according to any of claims 1 to 4 as semiconductors or charge transport materials, as thin-film transistors (TFTs), or in semiconductor components for organic light-emitting diodes (OLEDs), for photovoltaic components or in sensors, as an electrode material in batteries, as optical waveguides or for electrophotography applications.

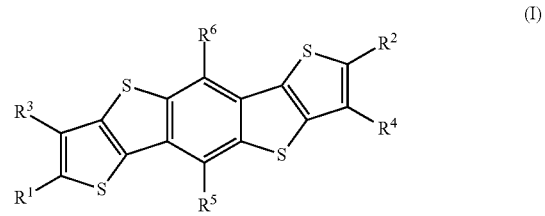

(I)

12 Claims, 2 Drawing Sheets

HIGH PERFORMANCE SOLUTION PROCESSABLE SEMICONDUCTOR BASED ON DITHIENO [2,3-D:2', 3'-D']BENZO[1,2-B:4,5-B'] DITHIOPHENE

CROSS-REFERENCE TO RELATED APPLICATIONS

This application is a US National Stage Application of PCT/EP2009/057985, filed on Jun. 25, 2009, the text of which is incorporated by reference, and claims priority to European Patent Application No. 08159525.8, filed on Jul. 2, 2008, the text of which is also incorporated by reference.

BACKGROUND OF THE INVENTION

The present invention relates to dithienobenzothiophenes, to a process for their preparation and to their use as semiconductors or charge transport materials.

The formidable building block for the development of (micro)electronics during the last one-half of the $20^{th}$ century is the field-effect transistor (FET) based on inorganic electrodes, insulators, and semiconductors. These materials have proven to be reliable, highly efficient, and with performance that increases periodically according to the well-known Moore's law. Rather than competing with conventional silicon technologies, an organic FET (OFET) based on molecular and polymeric materials may find large scale applications in low-performance memory elements as well as integrated optoelectronic devices, such as pixel drive and switching elements in active-matrix organic light-emitting diode displays, RFID tags, smart-ID tags, and sensors.

The use of organic semiconductors in OTFTs has some advantages over the inorganic semiconductors used to date. They can be processed in any form, from the fiber to the film, exhibit a high mechanical flexibility, can be produced at low cost and have a low weight. The significant advantage is, however, the possibility of producing the entire semiconductor component by deposition of the layers from solution on a polymer substrate at atmospheric pressure, for example by printing techniques, such that inexpensively producible FETs are obtained.

Among the organic semiconductors used in OFETs, oligothiophenes, polythiophenes, acenes, rylenes, and phthalocyanenes are the most investigated. For instance, the first report on a polyheterocycle-based FET was on polythiophene. In addition, poly(3-hexyl)thiophene and α,ω-dialkyloligothiophenes were the first high-mobility polymer and small molecules, respectively. Over the years, chemical modifications of these compounds, including variations in ring-to-ring connectivity and substitution pattern, have resulted in a considerable number of electro-active materials.

The performance of the electronic devices depends essentially on the mobility of the charge carriers in the semiconductor material and the ratio between the current in the on-state and the off-state (on/off ratio). An ideal semiconductor therefore has a minimum conductivity in the switched-off state and a maximum charge carrier mobility in the switched-on state (mobility above $10^{-3}$ $cm^2V^{-1}s^{-1}$ on/off ratio above $10^2$). In addition, the semiconductor material has to be relatively stable to oxidation, i.e. has to have a sufficiently high ionization potential, since its oxidative degradation reduces the performance of the component.

One of the most widely used organic p-type semiconductors is pentacene which typically shows mobilities greater than 1.5 $cm^2/Vs$. Due to its polymorphic structure and its need to be deposited from the vapour phase, this acene derivative complicates device studies (Lin et al. IEEE Trans. Electron Devices 1997, 44, 1325). Solution processable derivatives of pentacene have been reported, exhibiting charge carrier mobilities of 1.8 $cm^2/Vs$ (Park et al. 2005 Int. Electron. Dev. Mtg. Technol. Digest 2006, 113). Nevertheless the general instability of the higher acenes hampers the wide utilization in final applications.

WO 2008/026602 discloses unsubstituted and substituted [1]benzothieno[3,2-b][1]benzothiophene as organic semiconductors. These compounds are substituted in 3,8 position, and, respectively, in 2,7 position, with n-$C_6H_{13}$, n-$C_6F_{13}$, phenyl, pentafluorophenyl, p-trifluoromethylphenyl and diphenylyl. Disclosed is also unsubstituted Naphtho[2,3-b] naphtho[2'3':4,5]thieno[2,3-d]thienophene.

JP 2008-10541 A discloses substituted benzo[1",2":4,5; 4",5":4',5]dithieno[3,2-b:3',2'-b']bis[1]benzothiophene which is substituted in 6,13-position with tris(1-methylethyl)silylethinyl and with 4-hexyl-2,6-diisopropylphenyl respectively. FETs utilising components of this structure class are reported to reach a maximum mobility of 0.47 $cm^2/Vs$.

For the reported, high performance small molecule semiconductors the reaction routes are lengthy and often low yielding.

BRIEF SUMMARY OF THE INVENTION

It is an object of the present invention to provide novel compounds for use as organic semiconductor material, which are easy to synthesize, have significantly higher mobilities, show a good oxidation stability, and can be processed readily.

This object is achieved by dithienobenzodithiophenes of general formula (I)

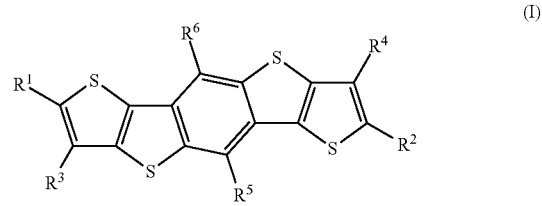

in which
$R^1$ to $R^6$ are each independently selected from a) H, b) halogen, c) —CN, d) —$NO_2$, e) —OH, f) a $C_{1-20}$ alkyl group, g) a $C_{2-20}$ alkenyl group, h) a $C_{2-20}$ alkynyl group, i) a $C_{1-20}$ alkoxy group, j) a $C_{1-20}$ alkylthio group, k) a $C_{1-20}$ haloalkyl group, l) a —Y—$C_{3-10}$ cycloalkyl group, m) a —Y—$C_{6-14}$ aryl group, n) a —Y-3-12 membered cycloheteroalkyl group, or o) a —Y-5-14 membered heteroaryl group,
wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group is optionally substituted with 1-4 $R^7$ groups,
wherein $R^1$ and $R^3$ and $R^2$ and $R^4$ may also together form an aliphatic cyclic moiety.
$R^7$ is independently selected from a) halogen, b) —CN, c) —$NO_2$, d) oxo, e) —OH, f) —$NH_2$, g) —NH($C_{1-20}$ alkyl), h) —N($C_{1-20}$ alkyl)$_2$, i) N($C_{1-20}$ alkyl)-$C_{6-14}$ aryl, j) —N($C_{6-14}$ aryl)$_2$, k) —S(O)$_m$H, l) —S(O)$_m$—$C_{1-20}$ alkyl, m) —S(O)$_2$OH, n) —S(O)$_m$—O$C_{1-20}$ alkyl, o) —S(O)$_m$—O$C_{6-14}$ aryl, p) —CHO, q) —C(O)—$C_{1-20}$ alkyl, r)

—C(O)—C$_{6-14}$ aryl, s) —C(O)OH, t) —C(O)—OC$_{1-20}$ alkyl, u) —C(O)—OC$_{6-14}$ aryl, v) —C(O)NH$_2$, w) —C(O)NH—C$_{1-20}$ alkyl, x) —C(O)N(C$_{1-20}$ alkyl)$_2$, y) —C(O)NH—C$_{6-14}$ aryl, z) —C(O)N(C$_{1-20}$ alkyl)-C$_{6-14}$ aryl, aa) —C(O)N(C$_{6-14}$ aryl)$_2$, ab) —C(S)NH$_2$, ac) —C(S)NH—C$_{1-20}$ alkyl, ad) —C(S)N(C$_{1-20}$ alkyl)$_2$, ae) —C(S)N(C$_{6-14}$ aryl)$_2$, af) —C(S)N(C$_{1-20}$ alkyl)-C$_{6-14}$ aryl, ag) —C(S)NH—C$_{6-14}$ aryl, ah) —S(O)$_m$NH$_2$, ai) —S(O)$_m$NH(C$_{1-20}$ alkyl), aj) —S(O)$_m$N(C$_{1-20}$ alkyl)$_2$, ak) —S(O)$_m$NH(C$_{6-14}$ aryl), al) —S(O)$_m$N(C$_{1-20}$ alkyl)-C$_{6-14}$ aryl, am) —S(O)$_m$N(C$_{6-14}$ aryl)$_2$, an) —SiH$_3$, ao) —SiH(C$_{1-20}$ alkyl)$_2$, ap) —SiH$_2$(C$_{1-20}$ alkyl), aq) —Si(C$_{1-20}$ alkyl)$_3$, ar) a C$_{1-20}$ alkyl group, as) a C$_{2-20}$ alkenyl group, at) a C$_{2-20}$ alkynyl group, au) a C$_{1-20}$ alkoxy group, av) a C$_{1-20}$ alkylthio group, aw) a C$_{1-20}$ haloalkyl group, ax) a C$_{3-10}$ cycloalkyl group, ay) a C$_{6-14}$ aryl group, az) a haloaryl group, ba) a 3-12 membered cycloheteroalkyl group, or bb) a 5-14 membered heteroaryl group, Y is independently selected from divalent a C$_{1-6}$ alkyl group, a divalent C$_{1-6}$ haloalkyl group, or a covalent bond; and m is independently selected from 0, 1, or 2.

The advantage of the dithienobenzodithiophenes of the invention is a simple, high yielding synthetic route towards a solution processable, stable organic semiconductor. Starting from commercially available materials the target structure class can be obtained in only three reaction steps with an overall yield of up to 50% (without optimisation). Single compounds from the described structure class show charge carrier mobilites of 1.4 cm$^2$/Vs and a current on/off ratio of 10$^8$.

The present invention further provides for the use of the dithienobenzodithiophenes according to the present invention as semiconductors or charge transport materials, especially in optical, electrooptical or electronic components, as thin-film transistors, especially in flat visual display units, or for radiofrequency identification tags (RFID tags) or in semiconductor components for organic light-emitting diodes (OLEDs), such as electroluminescent displays or backlighting for liquid-crystalline displays, for photovoltaic components or in sensors, as electrode material in batteries, as optical wave-guides, for electrophotography applications such as electrophotographic recording.

The present invention further provides optical, electrooptical or electronic components comprising the dithienobenzodithiophenes according to the present invention. Such components may be, for example, FETs, integrated circuits (ICs), TFTs, OLEDs or alignment layers.

DETAILED DESCRIPTION OF THE INVENTION

Figure 1A:
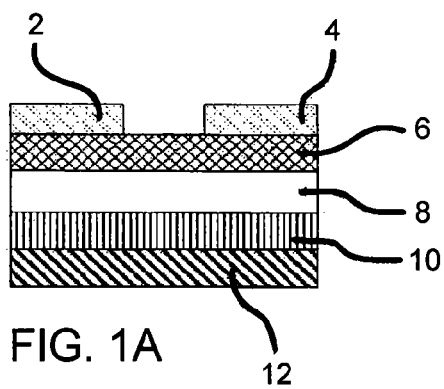
FIGS. 1a-1d illustrate the four common types of OFET structures.
Figure 1B:
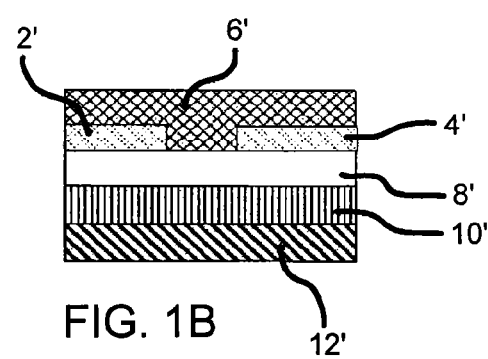
Figure 1C:
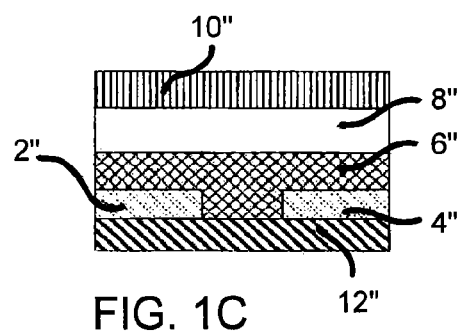
Figure 1D:
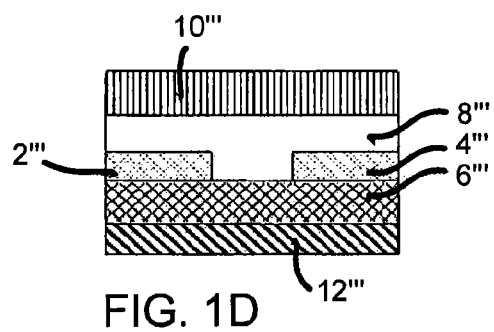

The dithienobenzodithiophenes according to the present invention are suitable particularly as semiconductors, since they have the mobilities required for this purpose. The introduction of alkyl groups improves its solubility and hence its processability as solutions.

As used herein, "field effect mobility" or "mobility" refers to a measure of the velocity with which charge carriers induced by an external stimulus such as an electric field, for example, holes (or units of positive charge) in the case of a p-type semiconducting material and electrons in the case of an n-type semiconducting material, move through the material under the influence of an electric field.

A "cyclic moiety" can include one or more (e.g., 1-6) carbocyclic or heterocyclic rings. In embodiments where the cyclic moiety is a polycyclic moiety, the polycyclic system can include one or more rings fused to each other (i.e., sharing a common bond) and/or connected to each other via a spiro atom. The cyclic moiety can be a cycloalkyl group, a heterocycloalkyl group, and can be optionally substituted as described herein.

"Halo" or "halogen" refers to fluoro, chloro, bromo, and iodo, preferably fluoro, chloro or bromo.

"Alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), and the like. Alkyl groups preferably can have 1 to 30 carbon atoms, for example, 1-20 carbon atoms (i.e., C$_{1-20}$ alkyl group). Alkyl groups particularly preferably can have 1 to 6 carbon atoms, and can be referred to as a "lower alkyl group". Alkyl groups can be substituted or unsubstituted. An alkyl group is generally not substituted with another alkyl group, an alkenyl group, or an alkynyl group.

"Haloalkyl" refers to an alkyl group having one or more halogen substituents. A haloalkyl group preferably can have 1 to 20 carbon atoms, in particular 1 to 10 carbon atoms. Examples of haloalkyl groups include CF$_3$, C$_2$F$_5$, CHF$_2$, CH$_2$F, CCl$_3$, CHCl$_2$, CH$_2$C$_1$, C$_2$Cl$_5$, and the like. Perhaloalkyl groups, i.e., alkyl groups where all of the hydrogen atoms are replaced with halogen atoms (e.g., CF$_3$ and C$_2$F$_5$), are included within the definition of "haloalkyl." Haloalkyl groups that are not perhaloalkyl groups can be optionally substituted with 1-5 R$^5$ and R$^5$ is as defined under formula (I).

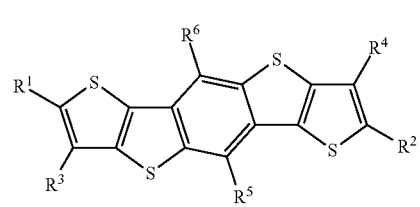

(I)

"Alkoxy" refers to —O-alkyl group. Examples of alkoxy groups include, but are not limited to, methoxy, ethoxy, propoxy (e.g., n-propoxy and isopropoxy), t-butoxy groups, and the like. The alkyl group in the —O-alkyl group can be optionally substituted with 1-5 R$^7$ and R$^7$ is as defined under formula (I).

"Alkylthio" refers to an .S-alkyl group. Examples of alkylthio groups include, but are not limited to, methylthio, ethylthio, propylthio (e.g., n-propylthio and isopropylthio), t-butylthio groups, and the like. The alkyl group in the —S-alkyl group can be optionally substituted with 1-5 R$^7$ and R$^7$ is as defined under formula (I).

"Arylalkyl" refers to an -alkyl-aryl group, where the arylalkyl group is covalently linked to the defined chemical structure via the alkyl group. An arylalkyl group is within the definition of an —Y—C$_{6-14}$ aryl group, where Y is as defined herein. An example of an arylalkyl group is a benzyl group (—CH$_2$—C$_6$H$_5$). An arylalkyl group can be optionally substituted, i.e., the aryl group and/or the alkyl group, can be substituted as disclosed herein.

"Alkenyl" refers to a straight-chain or branched alkyl group having one or more carbon-carbon double bonds. Preferred alkenyl groups are ethenyl, propenyl, butenyl, pentenyl, hexenyl, butadienyl, pentadienyl, hexadienyl groups. The one or more carbon-carbon double bonds can be internal (such as in 2-butene) or terminal (such as in 1-butene). In various embodiments, an alkenyl group can have 2 to 30 carbon atoms, for example, 2 to 20 carbon atoms (i.e., $C_{2-20}$ alkenyl group). In some embodiments, alkenyl groups can be substituted as disclosed herein. An alkenyl group is generally not substituted with another alkenyl group, an alkyl group, or an alkynyl group.

"Alkynyl" refers to a straight-chain or branched alkyl group having one or more triple carbon-carbon bonds. Preferred alkynyl groups include ethynyl, propynyl, butynyl, pentynyl. The one or more triple carbon-carbon bonds can be internal (such as in 2-butyne) or terminal (such as in 1-butyne). In various embodiments, an alkynyl group can have 2 to 30 carbon atoms, for example, 2 to 20 carbon atoms (i.e., $C_{2-20}$ alkynyl group). In some embodiments, alkynyl groups can be substituted as disclosed herein. An alkynyl group is generally not substituted with another alkynyl group, an alkyl group, or an alkenyl group.

"Cycloalkyl" refers to a non-aromatic carbocyclic group including cyclized alkyl, alkenyl, and alkynyl groups. A preferred cycloalkyl group can have 3 to 20 carbon atoms, for example, 3 to 14 carbon atoms (i.e., $C_{3-14}$ cycloalkyl group). A cycloalkyl group can be monocyclic (e.g., cyclohexyl) or polycyclic (e.g., containing fused, bridged, and/or Spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. Cycloalkyl groups can be substituted as disclosed herein.

"Heteroatom" refers to an atom of any element other than carbon or hydrogen and includes, for example, nitrogen, oxygen, silicon, sulfur, phosphorus, and selenium.

"Cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 20 ring atoms, for example, 3 to 14 ring atoms (i.e., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). Nitrogen or phosphorus atoms of cycloheteroalkyl groups can bear a substituent, in particular an alkyl group. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Preferred cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl. Cycloheteroalkyl groups can be substituted or unsubstituted.

"Aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. Preferably an aryl group can have from 6 to 16 carbon atoms in its ring system (e.g., $C_{6-16}$ aryl group), which can include multiple fused rings. Particularly preferably a polycyclic aryl group can have from 8 to 16 carbon atoms. Preferred aryl groups having only aromatic carbocyclic ring(s) include phenyl, 1-naphthyl (bicyclic), 2-naphthyl (bicyclic), anthracenyl (tricyclic), phenanthrenyl (tricyclic). Preferred polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Further preferred aryl groups include benzodioxanyl, benzodioxolyl, chromanyl, indolinyl groups, and the like. In some embodiments, aryl groups can be substituted as disclosed herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted or unsubstituted.

"Heteroaryl" refers to an aromatic monocyclic or polycyclic ring system containing at least one ring heteroatom. The heteroatom is preferably selected from oxygen (O), nitrogen (N), sulfur (S), silicon (Si), and selenium (Se) or a polycyclic ring system without being restricted thereto. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. Preferably a heteroaryl group can have from 5 to 16 ring atoms and contain 1-5 ring heteroatoms (i.e., 5-16 membered heteroaryl group). Particular examples of heteroaryl groups include, for example, the 5- or 6-membered monocyclic and 5-6 bicyclic ring systems shown below:

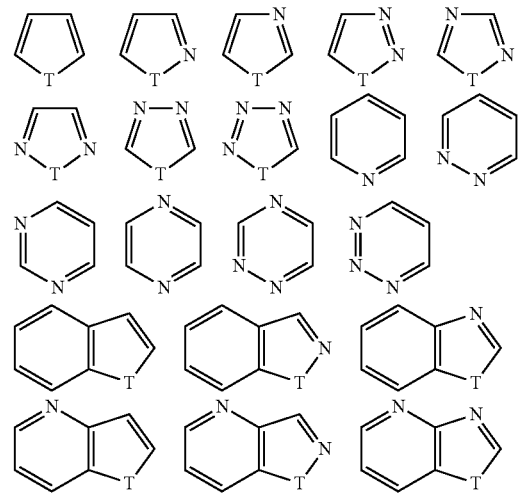

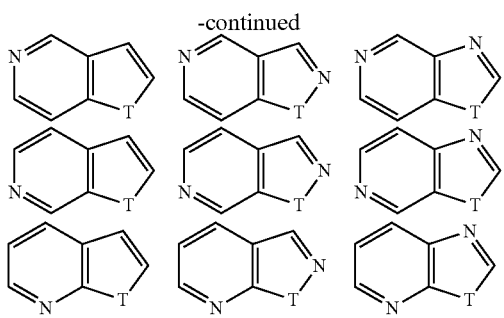

where T is O, S, NH, N-alkyl, N-aryl, N-(arylalkyl) (e.g., N-benzyl), SiH$_2$, SiH-(alkyl), Si(alkyl)$_2$, SiH-(arylalkyl), Si-(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as disclosed herein.

Compounds of the present teachings can include a "divalent group" defined herein as a linking group capable of forming a covalent bond with two other moieties. For example, compounds of the present teachings can include a divalent C$_{1-20}$ alkyl group, such as, for example, a methylene group.

Preferred dithienobenzodithiophenes are those of the formula (I)
in which
R$^1$ to R$^6$ are each independently selected from a) H, f) a C$_{1-20}$ alkyl group, i) a C$_{1-20}$ alkoxy group, m) a —Y—C$_{6-14}$ aryl group, as defined above.

More preferred dithienobenzodithiophenes are those of the formula (I)
in which
R$^1$ to R$^4$ are each independently selected from a) H, f) a C$_{1-20}$ alkyl group, i) a C$_{1-20}$ alkoxy group, m) a —Y—C$_{6-14}$ aryl group, as defined above, and
R$^5$ and R$^6$ are hydrogen.

Particularly preferred dithienobenzodithiophenes are those of the formula (I)
in which
R$^1$ and R$^2$ are each independently selected from a) H, f) a C$_{1-20}$ alkyl group, i) a C$_{1-20}$ alkoxy group, m) a —Y—C$_{6-14}$ aryl group, as defined above, and
R$^3$ to R$^6$ are hydrogen.

Particularly preferred substituents R$^1$ to R$^6$ are for R$^1$ and R$^2$ a C$_{1-20}$ alkyl group and for R$^3$ to R$^6$ hydrogen.

Dithienobenzodithiophenes of the present teachings can be prepared in accordance with the procedures outlined in Scheme 1 below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The dithienobenzodithiophenes of the formula (I) can preferably be prepared using the following reaction scheme 1:

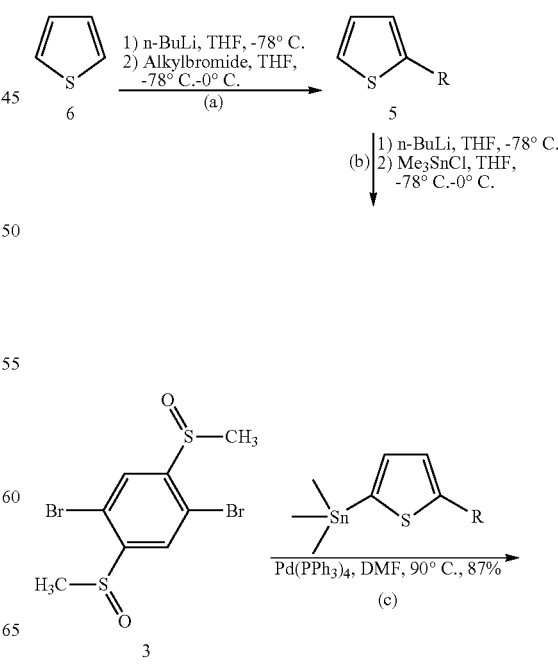

-continued

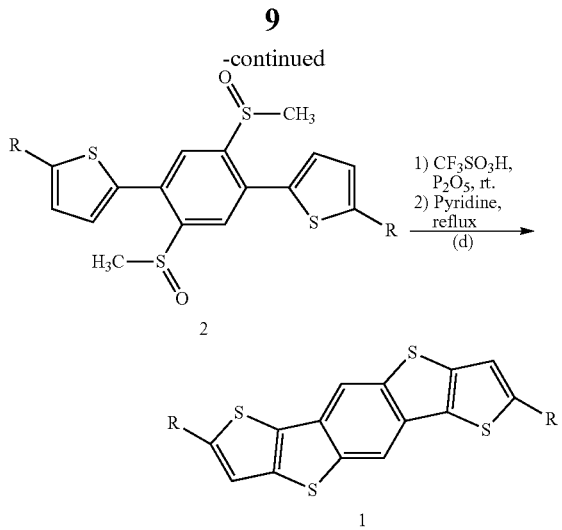

Steps (a), (b), (c) and (d) are described in:
(a) van Breemen et al. J. Am. Chem. Soc. 2006, 128, 2336-2345;
(b) Qin et al. J. Am. Chem. Soc. 2004, 126, 7015-7018;
(c) Zhao et al. J. Org. Chem. 2007, 72, 6364-6371;
(d) Sirringhaus et al. J. Mater. Chem. 1999, 9, 2095.

Compound 5 may be commercially available, depending on the nature of R.

The invention comprises both the oxidized and the reduced forms of the compounds according to the present invention. Either a deficiency or an excess of electrons leads to the formation of a delocalized ion which has a high conductivity. This can be done by doping with customary dopants. Dopants and doping processes are common knowledge and are known, for example, from EP-A 0 528 662, U.S. Pat. No. 5,198,153 or WO 96/21659. Suitable doping processes comprise, for example, doping with a doping gas, electrochemical doping in a solution comprising the dopant, by thermal diffusion and by ion implantation of the dopant into the semiconductor material.

In the case of use of electrons as charge carriers, preference is given to using halogens (e.g. $I_2$, $Cl_2$, $Br_2$, ICl, $ICl_3$, Ibr and IF), Lewis acids (e.g. $PF_5$, $AsF_5$, $SbF_5$, $BF_3$, $BCl_3$, $SbCl_5$, $BBr_3$ and $SO_3$), inorganic acids (e.g. HF, HCl, $HNO_3$, $H_2SO_4$, $HClO_4$, $FSO_3H$ and $ClSO_3H$), organic acids or amino acids, transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (where Ln is a lanthanoid)), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of different sulfonic acids such as aryl-$SO_3^-$. In the case of use of holes as charge carriers, as dopants, for example, are cations (e.g. $H^+$, $Li^+$, $Na^+$, $K^+$, $Rb^+$ and $Cs^+$), alkali metals (e.g. Li, Na, K, Rb, and Cs), alkaline earth metals (e.g. Ca, Sr and Ba), $O_2$, $XeOF_4$, ($NO_2^+$) ($SbF_6$), ($NO_2^+$) ($SbCl_6^-$), ($NO_2^+$) ($BF_4^+$), $AgClO_4$, $H_2IrCl_6$, $La(NO_3)_3$, $FSO_2OOSO_2F$, Eu, acetylcholine, $R_4N^+$, $R_4P^+$, $R_6As^+$ and $R_3S^+$, where R is an alkyl group.

The conductive form of the dithienobenzodithiophenes according to the present invention can be used as an organic conductor, for example charge injection layers and ITO planarizing layers in organic light-emitting diodes (OLEDs), flat screens and touch screens, antistatic films, printed circuits and capacitors, without being restricted thereto.

The dithienobenzodithiophenes according to the present invention can be used to produce optical, electronic and semiconductor materials, especially as charge transport materials in field-effect transistors (FETs), for example as components of integrated circuits (ICs), ID tags or TFTs. Alternatively, they can be used in organic light-emitting diodes (OLEDs) in electroluminescent displays or as backlighting, for example liquid-crystal displays (LCDs), in photovoltaic applications or for sensors, for electrophotographic recording and other semiconductor applications.

Since the dithienobenzodithiophenes according to the present invention have good solubility, they can be applied to the substrates as solutions. Layers can therefore be applied with inexpensive processes, for example spin-coating or printing.

Suitable solvents or solvent mixtures comprise, for example, ether, aromatics and especially chlorinated solvents.

FETs and other components comprising semiconductor materials, for example diodes, can be used advantageously in ID tags or security labels in order to indicate authenticity and to prevent forgeries of valuable items such as banknotes, credit cards, identity documents such as ID cards or driving licenses or other documents with pecuniary advantage such as rubber stamps, postage stamps or tickets, etc.

Alternatively, the polymers according to the present invention can be used in organic light-emitting diodes (OLEDs), for example in displays or as backlighting for liquid-crystal displays (LCDs). Typically, OLEDs have a multilayer structure. A light-emitting layer is generally embedded between one or more electron- and/or hole-transporting layers. When an electrical voltage is applied, the electrons or holes can migrate in the direction of the emitting layer, where their recombination to the excitation and subsequent luminescence of the luminophoric compounds in the emitting layer. The polymers, materials and layers may, according to their electrical and optical properties, find use in one or more of the transport layers and/or emitting layers. When the compounds, materials or layers are electroluminescent or have electroluminescent groups or compounds, they are particularly suitable for the emitting layer.

Various deposition techniques, including deposition from the gas phase and various solution processing techniques, have been used with organic semiconductors. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. Micro dispensing is another non-contact method of printing. However, contact printing techniques have the advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like. Other solution processing techniques include, for example, spin coating, drop-casting, zone casting, dip coating, blade coating, or spraying.

Various articles of manufacture including electronic devices, optical devices, and optoelectronic devices, such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds disclosed herein also are within the scope of the present teachings as are methods of making the same.

The present teachings, therefore, further provide methods of preparing a semiconductor material. The methods can include preparing a composition that includes one or more compounds disclosed herein dissolved or dispersed in a liquid medium such as solvent or a mixture of solvents, depositing the composition on a substrate to provide a semiconductor material precursor, and processing (e.g. heating) the semiconductor precursor to provide a semiconductor material (e.g. a thin film semiconductor) that includes a compound disclosed herein. In various embodiments, the liquid medium is an organic solvent, an inorganic solvent such as water, or combinations thereof. In some embodiments, the composition can further include one or more additives independently selected from detergents, dispersants, binding agents, compatiblizing agents, curing agents, initiators, humectants, antifoaming agents, wetting agents, pH modifiers, biocides, and bacteriostats. For example, surfactants and/or other polymers (e.g., polystyrene, polyethylene, poly-alpha-methylstyrene, polyisobutene, polypropylene, polymethylmethacrylate, and the like can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone-casting, dip coating, blade coating, or spraying.

The present teachings further provide articles of manufacture such as the various devices described herein that include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., described in Yoon, M-H. et al., PNAS, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which materials of the present teachings are useful are photovoltaics or solar cells. Components of the present teachings can exhibit broad optical absorption and/or a very positively shifted reduction potential, making them desirable for such applications. Accordingly, the substances described herein can be used as a p-type semiconductor in a photovoltaic design, which includes an adjacent n-type semiconducting material that forms a p-n junction. The compounds can be in the form of a thin film semiconductor, which can be deposited on a substrate to form a composite. Exploitation of small molecules of the present teachings in such devices is within the knowledge of a skilled artisan.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 1 illustrates the four common types of OFET structures: top-contact bottom-gate structure (a), bottom-contact bottom-gate structure (b), bottom-contact top-gate structure (c), and top-contact top-gate structure (d). As shown in FIG. 1, an OFET can include a dielectric layer (e.g., shown as 8, 8', 8", and 8''' in FIGS. 1a, 1b, 1c, and 1d, respectively), a semiconductor layer (e.g., shown as 6, 6', 6", and 6''' in FIGS. 1a, 1b, 1c, and 1d, respectively), a gate contact (e.g., shown as 10, 10', 10", and 10''' in FIGS. 1a, 1b, 1c, and 1d, respectively), a substrate (e.g., shown as 12, 12', 12", and 12''' in FIGS. 1a, 1b, 1c, and 1d, respectively), and source and drain contacts (e.g., shown as 2, 2', 2", 2''', 4, 4', 4", and 4''' in FIGS. 1a, 1b, 1c, and 1d, respectively).

In certain embodiments, OTFT devices can be fabricated with the present compounds on doped silicon substrates, using $SiO_2$ as the dielectric, in top-contact geometries. In particular embodiments, the active semiconducting layer which incorporates at least a material of the present teachings can be deposited at room temperature or at an elevated temperature. In other embodiments, the active semiconducting layer which incorporates at least a compound of the present teachings can be applied by spincoating or printing as described herein. For top-contact devices, metallic contacts can be patterned on top of the films using shadow masks.

All quantitative data (percentages, ppm, etc.) are based on the weight, based on the total weight of the mixture; unless stated otherwise.

EXAMPLES

Preparation of Dithieno[2,3-d:2',3'-d']benzo[1,2-b:4,5-b']dithiophene

Example 1

Reaction scheme 1:

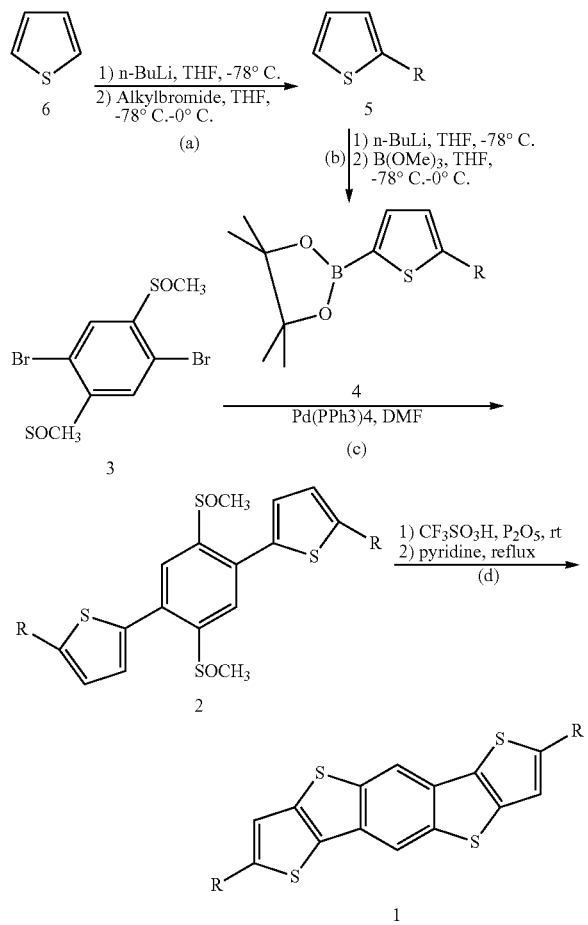

Synthesis of 4,4,5,5-tetramethyl-2-(5-pentylthiophen-2-yl)-1,3,2-dioxaborolane (4a)

To a cooled (−78° C.) mixture of 2-n-pentylthiophene (5.0 g, 32.1 mmol) and pinacol (11.5 g, 97.23 mmol) in anhydrous THF (60 mL) was added dropwise to a solution of n-BuLi (22.3 mL, 35.6 mmol) in hexane. The mixture was stirred at −78° C. for 10 minute. The reaction mixture was then brought to 0° C. and stirred for 1 h before cooling to −78° C. before the addition of triisopropyl borate (7.3 g, 38.9 mmol) in THF (24 mL) using a dropping funnel. The mixture was slowly brought to room temperature while stirring overnight. The crude product was purified by flash chromatography (silica gel. eluent: hexane/EA) 10:1) to afford a reddish brown liquid 7.35 g (81.0%).

$^1$H NMR (CDCl$_3$) δ (ppm): 7.46 (d, 1H, J=3.6 Hz), 6.86 (d, 1H, J=3.6 Hz), 2.85 (t, 2H, J=7.6 Hz) 1.70-1.64 (m, 2H), 1.34-0.90 (m, 18H), 0.87 (t, 3H, J=7.2 Hz)

Synthesis of 5,5'-(2,5-bis(methylsulfinyl)-1,4-phenylene)bis(2-pentylthiophene) (2a)

1,4-dibromo-2,5-bis(methylsulfinyl)benzene 3 (1 g, 2.8 mmol) was added to a solution of 4,4,5,5-tetramethyl-2-(5-pentylthiophen-2-yl)-1,3,2-dioxaborolane (3.4 g, 12.2 mmol) in anhydrous THF (17 mL), and the resulting mixture was purged with nitrogen for 30 min. Pd(PPh$_3$)$_4$ (87 mg, 0.075 mmol) was then added, and the 15 reaction mixture was heated to 60° C. overnight. The mixture was extracted with dichloromethane and washed with brine. The filtrate was dried over Mg$_2$SO$_4$, filtered, and the solvent removed in vacuo. The crude product was purified by flash chromatography (silica gel, eluent: hexane/EA) 3:1) to afford 0.885 g (63%) of 2a.

$^1$H NMR (CDCl$_3$) δ (ppm): 8.13 (s, 2H), 7.08 (d, 2H, J=3.6 Hz), 6.80 (d, 2H, J=3.6 Hz), 2.84 (t, 4H, J=7.2 Hz), 2.62 (s, 6H), 1.74-1.70 (m, 4H), 1.38-1.35 (m, 6H), 0.92 (t, 6H, J=2.8 Hz)

Synthesis of Dithieno[2,3-d:2',3'-d']benzo[1,2-b:4,5-b']dithiophene (1a)

A round bottomed flask was filled with 5,5'-(2,5-bis(methylsulfinyl)-1,4-phenylene)bis(2-pentylthiophene) (2a) (885 mg, 1.7 mmol), phosphorus pentoxide (93 mg, 0.658 mmol) and trifluoromethanesulfonic acid (20 ml). The mixture was stirred for 72 h at room temperature to give a dark brown solution, which was then poured into ice-water (100 ml). The yellow precipitate was collected by suction filtration and dried under vacuum. The structure of this compound, which was insoluble in apolar organic solvents, was assumed to be the sulfonium salt. Demethylation of the solid was achieved by refluxing it in pyridine (132 ml) for 12 h. When the suspension was cooled to room temperature, a large volume of CH$_2$Cl$_2$ was added to extract the product. Dithieno[2,3-d:2',3'-d']benzo[1,2-b:4,5-b']dithiophene (1a) was thus obtained as off-white powder by Hexane as an eluent and recrystalise in dichloromethane (200 mg, 26%).

$^1$H NMR (CDCl$_3$) δ (ppm): 8.17 (s, 2H), 7.01 (s, 2H), 2.94 (t, 4H, J=7.6 Hz), 1.77-1.55 (m, 4H), 1.42-1.37 (m, 8H), 0.90 (t, 6H, J=6.8 Hz)

Example 2

Reaction scheme 2:

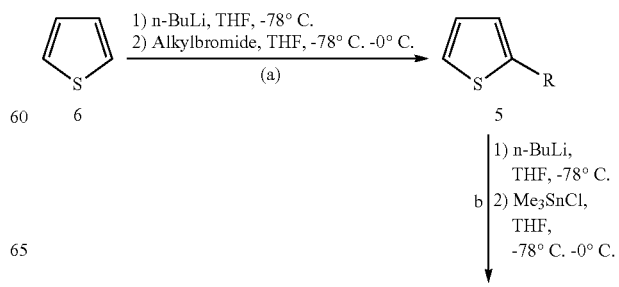

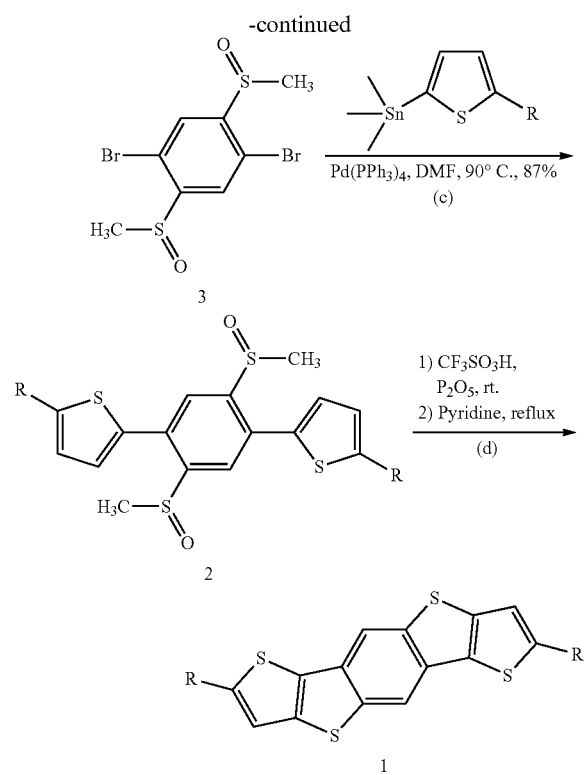

Synthesis of 2-hexyl-thiophene (5b)

To a cooled (−70° C.) mixture of thiophene (17.6 g, 0.21 mol) in anhydrous THF (100 mL) was added dropwise a solution of n-BuLi (137.5 ml, 1.6 M, 0.22 mol) in hexane. After stirring for 1 hour at 0° C., the mixture was cooled to −40° C. followed by addition of 1-hexylbromide (0.22 mol). The mixture was slowly heated to r.t. Water (250 mL) was added and the mixture was extracted with diethylether (3×150 mL). The combined organic fractions were dried over MgSO$_4$ and concentrated in vacuo. The product was purified by means of vacuum distillation. This product was prepared according to the general procedure and obtained as a colourless oil (26.5 g, 75%).

Synthesis of 5-hexyl-2-trimethylstannylthiophene (4b)

2-Hexylthiophene (23.0 g, 0.137 mol) was dissolved in 250 ml THF and n-BuLi (94 ml, 1.6 M in hexanes, 0.150 mol) was added dropwise at 0° C. The mixture was stirred at 0° C. for 1 h and then cooled down to −78° C. A solution of trimethyltin chloride (32.8 g, 0.164 mol) in 100 ml THF was added dropwise. The mixture was allowed to warm slowly to room temperature and stirred for 2 h. After quenching with ice water and aqueous work-up, the product was distilled at 108° C. under high vacuum. 5-Hexyl-2-trimethylstannylthiophene was obtained as a colourless liquid (40.8 g, 90% yield).

Synthesis of 5,5'-(2,5-bis(methylsulfinyl)-1,4-phenylene)bis(2-hexylthiophene) (2b)

1,4-dibromo-2,5-bis(methylsulfinyl)benzene 3 (0.900 g, 2.5 mmol) was added to a solution of 4b (1.82 g, 5.5 mmol) in anhydrous DMF (30 mL), and the resulting mixture was purged with Ar for 30 min. Pd(PPh$_3$)$_4$ (87 mg, 0.075 mmol) was then added, and the reaction mixture was heated to 80° C. overnight. Excess DMF was removed under high vacuum, and the residue was dissolved in ethyl acetate and treated with 10% aqueous KF. The mixture was filtered through a pad of Celite. The filtrate was dried over Mg$_2$SO$_4$, filtered, and the solvent removed in vacuo. The crude product was purified by flash chromatography (silica gel, eluent:hexane/THF) 1:1) to afford 1 g (75%) of 2b.

Synthesis of dithieno[2,3-d:2',3'-d']benzo[1,2-b:4,5-b']dithiophene (1b)

A 10 ml round bottomed flask was filled with 5,5'-(2,5-bis(methylsulfinyl)-1,4-phenylene)bis(2-hexylthiophene) (2b) (200 mg, 0.53 mmol), phosphorus pentoxide (28 mg, 0.2 mmol) and trifluoromethanesulfonic acid (6 ml). The mixture was stirred for 72 h at room temperature to give a dark brown solution, which was then poured into ice-water (100 ml). The yellow precipitate was collected by suction filtration and dried under vacuum. The structure of this compound, which was insoluble in apolar organic solvents, was assumed to be the sulfonium salt. Demethylation of the solid was achieved by refluxing it in pyridine (40 ml) for 12 h. When the suspension was cooled to room temperature, a large volume of CH$_2$Cl$_2$ was added to extract the product. Dithieno[2,3-d:2',3'-d']benzo[1,2-b:4,5-b']dithiophene (1b) was thus obtained as off-white powder by Hexane as an eluent (120 mg, 70%).

Example 3

Synthesis of 2-propyl-5-trimethylstannylthiophene (4c)

2-propylthiophene (5.0 g, 39.6 mmol) was dissolved in 160 ml THF and n-BuLi (27 ml, 1.6 M in hexanes, 43.6 mmol) was added dropwise at 0° C. The mixture was stirred at 0° C. for 1 h and then cooled down to −78° C. A solution of trimethyltin chloride (8.679 g, 43.6 mmol) in 50 ml THF was added dropwise. The mixture was allowed to warm slowly to room temperature and stirred for 2 h. After quenching with ice water and aqueous work-up, the product was obtained as a light brown liquid (10.1348 g, 88.6% yield).

$^1$H NMR (CDCl$_3$) δ (ppm): 7.02-7.01 (m, 1H), 6.91-6.90 (m, 1H), 2.84 (t, 2H, J=7.6 Hz), 1.74-1.69 (m, 4H), 0.986 (t, 6H, J=7.6 Hz), 0.341 (s, 9H)

Synthesis of 5,5'-(2,5-bis(methylsulfinyl)-1,4-phenylene)bis(2-propylthiophene) (2c)

1,4-dibromo-2,5-bis(methylsulfinyl)benzene 3 (2.60 g, 7.21 mmol) was added to a solution of 2-propyl-5-trimethylstannylthiophene (5.0 g, 17.3 mmol) in anhydrous Toulene (48 mL), and the resulting mixture was purged with nitrogen for 30 min. Pd(PPh$_3$)$_4$ (0.833 g, 0.072 mmol) was then added, and the reaction mixture was heated to 100° C. overnight. Excess Toulene was removed under high vacuum, and the residue was dissolved in ethyl acetate and treated with 10% aqueous KF. The mixture was filtered through a pad of Celite. The filtrate was dried over Mg2SO$_4$, filtered, and the solvent removed in vacuo. The crude product was purified by flash chromatography (silica gel, eluent:hexane/EA) 2:1) to afford 2.63 g (81%) of 2c.

$^1$H NMR (CDCl$_3$) δ (ppm): 8.13 (s, 2H), 7.08 (d, 2H, J=3.6 Hz), 6.80 (d, 2H, J=3.6 Hz, 2.76 (t, 4H, J=7.2 Hz), 2.50 (s, 6H), 1.70-1.65 (m, 4H), 0.94 (t, 6H, J=7.2 Hz)

Synthesis of dithieno[2,3-d:2',3'-d']benzo[1,2-b:4,5-b']dithiophene (1c)

A round bottomed flask was filled with 5,5'-(2,5-bis(methylsulfinyl)-1,4-phenylene)bis(2-propylthiophene) (2c) (1.0 g, 2.2 mmol), phosphorus pentoxide (0.1 g, 0.703 mmol) and trifluoromethanesulfonic acid (20 ml). The mixture was stirred for 72 h at room temperature to give a dark brown solution, which was then poured into ice-water (120 ml). The yellow precipitate was collected by suction filtration and dried under vacuum. The structure of this compound, which was insoluble in apolar organic solvents, was assumed to be the sulfonium salt. Demethylation of the solid was achieved by refluxing it in pyridine (167 ml) for 12 h. When the suspension was cooled to room temperature, a large volume of $CH_2Cl_2$ was added to extract the product. Dithieno[2,3-d:2',3'-d']benzo[1,2-b:4,5-b']dithiophene (1c) was thus obtained as off-white powder by hexane as an eluent and recrystalised in dichloromethane (370 mg, 43%).

$^1$H NMR (CDCl$_3$) δ (ppm): 8.17 (s, 2H), 7.01 (s, 2H), 2.93 (t, 4H, J=7.6 Hz), 1.83-1.77 (m, 4H), 1.04 (t, 6H, J=7.2 Hz)

Example 4

Preparation of OFETs Using Compounds 1-4

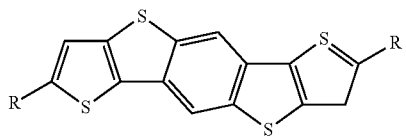

Compound
1: R=CH$_3$
2: R=C$_6$H$_{13}$
3: R=2-ethylhexyl
4: R=C$_9$H$_{19}$

For all devices, heavily doped silicon wafers with a 150 nm thick thermally grown silicon dioxide layer are used as substrates. For bottom gate, bottom contact OFETs, source and drain electrodes with channel lengths of 10 μm and widths of 5 mm are defined on top of the SiO$_2$ by conventional photolithography, followed by Cr/Au evaporation to a height of 2/40 nm.

For bottom gate, top contact OFETs, source and drain electrodes with channel lengths of 25 μm and widths of 290 μm are defined by a shadow mask, followed by Au evaporation to a height of 80 nm.

To deal with interface trapping the dielectric is either used untreated or treated with phenyltriethoxysilane (PIES) or hexamethyldisilazane (HMDS).

Here, PIES is deposited via immersing the substrates in a 0.1 vol-% THF solution for two hours, followed by a thermal treatment at 120° C. for two hours. HMDS is deposited out of the gas phase at 120° C. for three hours.

To influence the charge carrier injection from the electrodes into the semiconductor and/or the other way around, different thiols (e.g. propanethiol, octanethiol, hexadecanethiol, 4-nitrobenzenethiol, perfluorodecanethiol, pentafluoro-benzenethiol) are used to cover the electrodes via immersing the substrates in a 0.1 vol % ethanol solution for 24 hours.

For the solution processing of the semiconductor common organic solvents like toluene, chloroform, THF, chlorobenzene or dichlorobenzene are used. Drop-casting and spin-coating, the annealing process and all electrical measurements are performed in a glovebox under nitrogen atmosphere, while dip-coating and zone-casting are proceed under ambient conditions. The device characteristics are measured with a Keithley 4200-SCS.

To show the potential of the semiconductor molecules, bottom gate, bottom contact OFETs were fabricated by spin-coating (4000 min$^{-1}$, 40 s) of compounds 1-4 solutions on untreated SiO$_2$ substrates with pentafluorobenzenethiol treated electrodes. Here, chlorobenzene was used for compound 1, because it is unsoluble in chloroform that was used for compounds 2-4. After annealing the sample at 100° C. for 30 min, hole mobilities of up to 0.1 cm$^2$ V$^{-1}$ s$^{-1}$ in the saturated regime and on/off ratios of up to 10$^7$ were obtained. The results are summarized in table 1.

Mobility

To allow comparison with other organic FETs, mobilities (μ) were calculated by standard field effect transistor equations. In traditional metal-insulator-semiconductor FETs (MISFETs), there is typically a linear and saturated regime in the $I_{SD}$ vs. $V_{SD}$ curves at different $V_G$ (where $I_{SD}$ is the source-drain saturation current, $V_{DS}$ is the potential between the source and drain, and $V_G$ is the gate voltage). At large $V_{SD}$, the current saturates and is given by:

$$(I_{SD})_{sat} = (WC_i/2L)\mu(V_G - V_t)^2 \tag{1}$$

where L and W are the device channel length and width, respectively, $C_i$ is the capacitance of the dielectric, and $V_t$ is the threshold voltage. Therefore, mobilities (μ) were calculated in the saturation regime by rearranging equation (1):

$$\mu_{sat} = (2I_{SD}L)/[WC_i(V_G - V_t)^2] \tag{2}$$

Figure 2:
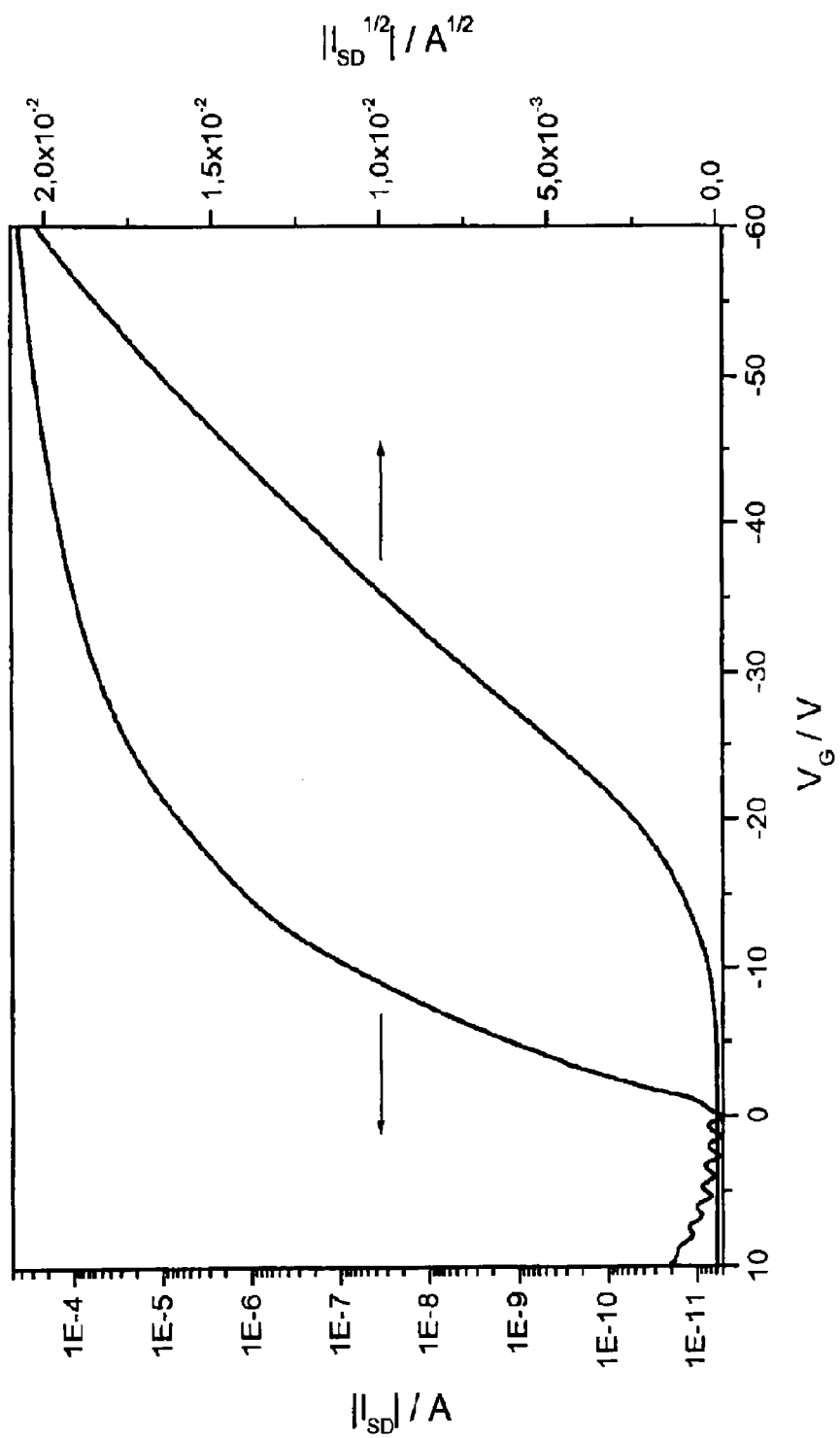
FIG. 2 depicts current that flows from a source to a drain electrode (I$_{SD}$) under a given V$_{SD}$.

Transfer Characteristic:

The current that flows from the source to the drain electrode ($I_{SD}$) under a given $V_{SD}$ increases almost quadratically with the increasing $V_G$ as shown in FIG. 2. In a typical representation of the transfer curve the square root of $I_{SD}$ is plotted against $V_G$. In such a graph the threshold voltage ($V_t$) can be estimated as the x intercept of the linear section of the plot of $V_G$ versus $(I_{DS})^{1/2}$

TABLE 1

FET characteristics of compound 1-4, spin-coated on pentafluorobenzenethiol treated bottom gate, bottom contact devices (values based on 5 transistors for each compound)

| | Compound 1 | Compound 2 | Compound 3 | Compound 4 |
|---|---|---|---|---|
| $\mu_{sat}$/cm$^2$ V$^{-1}$ s$^{-1}$ | 1.4 – 0.2 × 10$^{-3}$ | 0.1 – 0.07 | 1.5 – 0.7 × 10$^{-3}$ | 1.9 – 0.9 × 10$^{-3}$ |
| $I_{ON/OFF}$ | 10$^3$ | 10$^7$ | 10$^5$ | 10$^2$ |

The best result up to now was reached by dip-coating (0.5 µm s$^{-1}$) a 2 mg ml$^{-1}$ toluene solution of compound 2 on an untreated SiO$_2$ bottom gate, top contact device. The resulting film was highly crystalline with large domains extending over millimeters and exhibiting optical anisotropy. Hole mobilities of 1.4 cm$^2$ V$^{-1}$ s$^{-1}$ and on/off ratio of 10$^8$ were obtained as deduced from the transistor characteristics in the saturated regime illustrated in FIG. 2, which shows a typical FET transfer characteristic. The current between the source and drain electrode is plotted against the gate bias. In order to linearize the curve the gate bias was plotted against the square root of the source/drain current.

Example 5

Preparation of OTFTs

Solution Preparation:

For sample 1 to 4, the compounds were dissolved in xylene at a concentration of 2 or 5 mg/ml. The solutions were then heated to 50° C. before filtering the solutions using a with 0.45 µm filter.

For sample 5, 1 wt % of the compound and 0.75 wt % of polystyrene were dissolved in toluene. The solution was then heated at 50° C. before filtering using a 0.45 µm filter.

Device Fabrication:

Sample 1 to 3

To fabricate a bottom gate top contact device (BGTC), untreated Si substrate with 200 nm of thermally grown SiO$_2$ was used. The substrate was first heated to 70° C. or 80° C. before the solution was drop casted on it. The drop casting was done under ambient atmosphere. After the film was completely dried, 35 nm of gold source and drain electrodes were evaporated onto it. The channel width over length ratio was 70.

For sample 3, the film was annealed before gold deposition at 100° C. for 30 minutes under inert atmosphere.

Sample 4

To fabricate a bottom gate top contact device, untreated Si substrate with native SiO$_2$ was used. First, a crosslinkable polymer dielectric was spun onto substrate to achieve a thickness of 500 nm. It was then cured under UV for 2 minutes before dried at 100° C. for 2 minutes using a hotplate.

The substrate was then heated to 70° C. before the solution was drop casted on it. The drop casting was done under ambient atmosphere. After the film was completely dried, 35 nm of gold source and drain electrodes were evaporated onto it. The channel width over length ratio was 70.

Sample 5

To fabricate a bottom gate top contact device, untreated Si substrate with 200 nm of thermally grown SiO$_2$ was used. The substrate was dip coated at a pulling rate of 12.5 mm/min under ambient atmosphere. 35 nm of gold source and drain electrodes were then evaporated on to it. The channel width over length ratio was 70.

The device fabrication is summarized in table 1 below:

TABLE 1

| Sample | R in compound 1 | Dielectric | Organic solvent and concentration | Deposition Method | Deposition Condition | Remarks |
|---|---|---|---|---|---|---|
| 1 | C6 | Thermal grown SiO2 | Xylene (2 mg/ml) | Drop casting | Substrate temperature was kept at 70° C. in nonsaturated condition | |
| 2 | C5 | Thermal grown SiO2 | Xylene (2 mg/ml) | Drop casting | Substrate temperature was kept at 80° C. in nonsaturated condition | Annealed at 100° C. for 30 mins |
| 3 | C3 | Thermal grown SiO2 | Xylene (2 mg/ml) | Drop casting | Substrate temperature was kept at 80° C. in nonsaturated condition | |
| 4 | C5 | Polymer dielectric | Xylene (5 mg/ml) | Drop casting | Substrate temperature was kept at 70° C. in nonsaturated condition | |
| 5 | C6 | Thermal grown SiO2 | Toluene (1 wt %) | Dip coating | Pulling speed was set at 12.5 mm/min | Solution was blended with 0.75 wt % atactic polystyrene |

Device characteristics were measured with a Keithley 4200-SCS. The results are summarized in table 2 below:

TABLE 2

| Sample | µ (cm$^2$/Vs) | V$_{th}$ | On/Off |
|---|---|---|---|
| 1 | 1.12E−01 | −35 | 7.65E05 |
| 2 | 1.35E−01 | 0 | 2.03E05 |
| 3 | 1.98E−01 | 0 | 1.25E06 |
| 4 | 5.26E−02 | −10 | 1.94E04 |
| 5 | 1.71E−01 | −5 | 1.12E05 |

The invention claimed is:
1. A dithienobenzodithiophene of general formula (I)

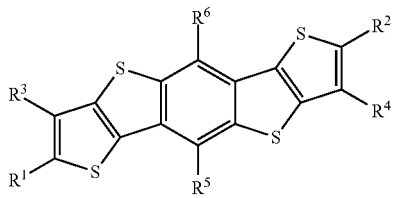

where
R' to R" are each independently selected from the group consisting of
a) H,
b) halogen,
c) —CN,
d) —NO$_2$,
e) —OH,
f) a C$_{1-20}$ alkyl group,
g) a C$_{2-20}$ alkenyl group,
i) a C$_{1-20}$ alkoxy group,
j) a C$_{1-20}$ alkylthio group,
k) a C$_{1-20}$ haloalkyl group,
l) a —Y—C$_{3-10}$ cycloalkyl group,
m) a —Y—C$_{6-14}$ aryl group,
n) a —Y-3-12 membered cycloheteroalkyl group, and
o) a —Y-5-14 membered heteroaryl group,
wherein
each of the C$_{1-20}$ alkyl group,
  the C$_{2-20}$ alkenyl group,
  the C$_{3-10}$ cycloalkyl group,
  the C$_{6-14}$ aryl group,
  the 3-12 membered cycloheteroalkyl group, and
  the 5-14 membered heteroaryl group
is optionally substituted with 1-4 R$^7$ groups,
R$^1$ and R$^3$ and R$^2$ and R$^4$ may also together form an aliphatic cyclic moiety,
R$^7$ is independently selected from the group consisting of
a) halogen,
b) —CN,
c) —NO$_2$,
d) oxo,
e) —OH,
f) —NH$_2$,
g) —NH(C$_{1-20}$ alkyl),
h) —N(C$_{1-20}$ alkyl)$_2$,
i) —N(C$_{1-20}$ alkyl)-C$_{6-14}$ aryl,
j) —N(C$_{6-14}$ aryl)$_2$,
k) —S(O)$_m$H,
l) —S(O)$_m$—C$_{1-20}$ alkyl,
m) —S(O)$_2$OH,
n) —S(O)$_m$—OC$_{1-20}$ alkyl,
o) —S(O)$_m$—OC$_{6-14}$ aryl,
p) —CHO,
q) —C(O)—C$_{1-20}$ alkyl,
r) —C(O)—C$_{6-14}$ aryl,
s) —C(O)OH,
t) —C(O)—OC$_{1-20}$ alkyl,
u) —C(O)—OC$_{6-14}$ aryl,
v) —C(O)NH$_2$,
w) —C(O)NH—C$_{1-20}$ alkyl,
x) —C(O)N(C$_{1-20}$ alkyl)$_2$,
y) —C(O)NH—C$_{6-14}$ aryl,
z) —C(O)N(C$_{1-20}$ alkyl)-C$_{6-14}$ aryl,
aa) —C(O)N(C$_{6-14}$ aryl)$_2$,
ab) —C(S)NH$_2$,
ac) —C(S)NH—C$_{1-20}$ alkyl,
ad) —C(S)N(C$_{1-20}$ alkyl)$_2$,
ae) —C(S)N(C$_{6-14}$ aryl)$_2$,
af) —C(S)N(C$_{1-20}$ alkyl)- C$_{6-14}$ aryl,
ag) —C(S)NH—C$_{6-14}$ aryl,
ah) —S(O)$_m$NH$_2$,
ai) —S(O)$_m$NH(C$_{1-20}$ alkyl),
aj) —S(O)$_m$N(C$_{1-20}$ alkyl)$_2$,
ak) —S(O)$_m$NH(C$_{6-14}$ aryl),
al) —S(O)$_m$N(C$_{1-20}$ alkyl)-C$_{6-14}$ aryl,
am) —S(O)$_m$N(C$_{6-14}$ aryl)$_2$,
an) —SiH$_3$,
ao) —SiH(C$_{1-20}$ alkyl)$_2$,
ap) —SiH$_2$(C$_{1-20}$ alkyl),
aq) —Si(C$_{1-20}$ alkyl)$_3$,
ar) a C$_{1-20}$ alkyl group,
as) a C$_{2-20}$ alkenyl group,
at) a C$_{2-20}$ alkynyl group,
au) a C$_{1-20}$ alkoxy group,
av) a C$_{1-20}$ alkylthio group,
aw) a C$_{1-20}$ haloalkyl group,
ax) a C$_{3-10}$ cycloalkyl group,
ay) a C$_{6-14}$ aryl group,
az) a haloaryl group,
ba) a 3-12 membered cycloheteroalkyl group, and
bb) a 5-14 membered heteroaryl group,
Y is independently selected from the group consisting of
  divalent a C$_{1-6}$ alkyl group,
  a divalent C$_{1-6}$ haloalkyl group, and
  a covalent bond; and
m is independently selected from 0, 1, or 2.
2. The dithienobenzodithiophene according to claim 1, wherein R$^1$ to R$^6$ are each independently selected from the group consisting of
a) H,
f) a C$_{1-20}$ alkyl group,
i) a C$_{1-20}$ alkoxy group, and
m) a —Y—C$_{6-14}$ aryl group.
3. The dithienobenzodithiophene according to claim 1, wherein R$^5$ and R$^6$ are hydrogen.
4. The dithienobenzodithiophene according to claim 1, wherein R$^3$ to R$^6$ are hydrogen.
5. A composition comprising one or more dithienobenzodithiophenes of claim 1, wherein the composition is dissolved or dispersed in a liquid medium.
6. A thin film semiconductor comprising one or more dithienobenzodithiophenes of claim 1.
7. A composite comprising a substrate and the thin film semiconductor of claim 6, wherein the composite is deposited on the substrate.
8. A process for preparation of a composite comprising a substrate and a thin film semiconductor comprising one or more dithienobenzodithiophenes of claim 1, comprising
  dissolving the dithienobenzodithiophene in a liquid medium to form a solution,
  depositing the solution on a substrate, and
  removing the solvent to form a thin film semiconductor on the substrate.
9. The process according to claim 8, wherein the solution is deposited by spin coating, dipcoating, drop casting or printing.
10. A field effect transistor device comprising the thin film semiconductor of claim 6 or the composite of claim 7.
11. A photovoltaic device comprising the thin film semiconductor of claim 6 or the composite of claim 7.
12. An organic light emitting diode device comprising the thin film semiconductor of claim 6 or the composite of claim 7.

* * * * *

UNITED STATES PATENT AND TRADEMARK OFFICE
CERTIFICATE OF CORRECTION

PATENT NO. : 8,367,717 B2
APPLICATION NO. : 13/002208
DATED : February 5, 2013
INVENTOR(S) : Marcel Kastler et al.

It is certified that error appears in the above-identified patent and that said Letters Patent is hereby corrected as shown below:

In the Claims

Column 21 line 15 "where $R'$ to $R''$ are each independently selected from" should read --where $R^1$ to $R^6$ are each independently selected from--

Signed and Sealed this
Twenty-fifth Day of June, 2013

Teresa Stanek Rea
*Acting Director of the United States Patent and Trademark Office*